(12) United States Patent
Choi et al.

(10) Patent No.: US 7,222,382 B2
(45) Date of Patent: May 29, 2007

(54) ELECTRON-MOTION TOOTHBRUSH

(76) Inventors: Joo A Choi, 101-205 Myeongji Apt. 575, Baekryeon-ri, Gurae-eup, Gurae-gun, Jeonrabuk-do (KR); Joo Ri Choi, 101-205 Myeongji Apt. 575, Baekryeon-ri, gurae-eup, gurae-gun, Jeonrabuk-do (KR)

( * ) Notice: Subject to any disclaimer, the term of this patent is extended or adjusted under 35 U.S.C. 154(b) by 371 days.

(21) Appl. No.: 10/483,816

(22) PCT Filed: Jul. 15, 2002

(86) PCT No.: PCT/KR02/01334

§ 371 (c)(1),
(2), (4) Date: Jan. 15, 2004

(87) PCT Pub. No.: WO03/007756

PCT Pub. Date: Jan. 30, 2003

(65) Prior Publication Data

US 2004/0168270 A1      Sep. 2, 2004

(30) Foreign Application Priority Data

Jul. 16, 2001 (KR) ............... 20-2001-0021489
May 8, 2002 (KR) ............... 10-2002-0025231

(51) Int. Cl.
*A61C 17/26* (2006.01)
(52) U.S. Cl. .......................................... 15/23
(58) Field of Classification Search .......... 15/23
See application file for complete search history.

(56) References Cited

U.S. PATENT DOCUMENTS

| 2,124,145 | A | * | 7/1938 | Merkel, Jr. ............... 15/23 |
| 3,015,833 | A | * | 1/1962 | Gilet ....................... 15/23 |
| 3,258,802 | A | | 7/1966 | Rodriguez |
| 3,512,202 | A | * | 5/1970 | Taylor ..................... 15/23 |
| 4,304,023 | A | | 12/1981 | O'Rourke |
| 4,603,448 | A | | 8/1986 | Middleton et al. |
| 4,845,796 | A | * | 7/1989 | Mosley ..................... 15/23 |
| 5,044,035 | A | | 9/1991 | Barradas |
| 5,428,855 | A | | 7/1995 | Li |
| 5,453,644 | A | * | 9/1995 | Yap et al. ............. 307/116 |
| 5,864,911 | A | | 2/1999 | Arnoux et al. |

FOREIGN PATENT DOCUMENTS

| CN | 2079948 U | | 7/1991 |
| CN | 2312679 Y | | 4/1999 |
| DE | 199 30 294 | | 1/2001 |
| EP | 488971 | * | 6/1992 |
| FR | 2662350 | * | 11/1991 |
| JP | 54-58472 U | | 9/1979 |
| JP | 07-177932 | | 7/1995 |
| JP | 08-019427 | | 1/1996 |
| JP | 08-280717 | | 10/1996 |

* cited by examiner

*Primary Examiner*—Mark Spisich
(74) *Attorney, Agent, or Firm*—Leydig, Voit & Mayer, Ltd.

(57) ABSTRACT

An electro-motion toothbrush includes a case containing a driving unit. First and second toothbrush support rods are flexible and rotated by the driving unit in directions opposite to each other. First and second toothbrush heads are connected to upper ends of the first and second toothbrush support rods, respectively. First and second toothbrush bristles are implanted along a lengthwise direction of the first and second toothbrush heads, interweave with each other, and not to cross each other during operation.

21 Claims, 15 Drawing Sheets

ELECTRON-MOTION TOOTHBRUSH

BACKGROUND OF THE INVENTION

1. Field of the Invention

The present invention relates to an electro-motion toothbrush, and, more particularly, to an electro-motion toothbrush in which first and second toothbrush heads are respectively coupled to first and second toothbrush support rods which are flexible and rotate in opposite directions and are capable of changing rotation directions. First and second toothbrush bristles are implanted in the first and second toothbrush heads, interweave with each other at upper and lower portions and are prevented from crossing each other during rotation. Accordingly, deformations of the toothbrush bristles are minimized and the toothbrush bristles can easily access the teeth. Also, the brushing direction of the toothbrush bristles changes according to the shape of teeth, thus providing improved cleaning performance and convenience in use.

2. Description of the Related Art

In general, a toothbrush is classified into a manual type and electro-motion type according to a driving method of toothbrush bristles. Recently, an electro-motion type adopting an electro-motion method that is easy to use is widely being used.

However, in a conventional electro-motion toothbrush, toothbrush bristles are perpendicularly implanted in a toothbrush head. Thus, after long use, the bristles are deformed and lie along the head, resulting in a damage to gums, which requires periodic replacement of the toothbrush head. Also, since the toothbrush bristles can hardly access areas between teeth, brushing both surfaces of a tooth is very inconvenient and the teeth cannot be cleaned accurately.

SUMMARY OF THE INVENTION

According to an aspect of the present invention, an electro-motion toothbrush comprising a case where a driving unit is installed, first and second toothbrush support rods which are flexible and rotated by the driving unit in directions opposite to each other, first and second toothbrush heads connected to upper ends of the first and second toothbrush support rods, respectively, and first and second toothbrush bristles which are implanted to interweave with each other along a lengthwise direction of the first and second toothbrush heads and not to cross each other during operation.

In the electro-motion toothbrush, the first and second toothbrush bristles are implanted in an at least one row spiral form.

In the electro-motion toothbrush, first and second toothbrush assemblies, formed by implanting the first and second toothbrush bristles in the first and second toothbrush heads, respectively, are similar to each other in the upper and lower sides and detachably coupled to the first and second toothbrush support rods, respectively.

The electro-motion toothbrush further comprises a light emitting unit which emits light outside the case.

The driving unit comprises a power source, first and second rotation gears which rotate by being engaged with each other by power from the power source, and first and second rotation support shafts, the first shaft connected and activated by having one ends fixed to the first and second rotation gears, respectively, and the other ends connected to the first and second toothbrush support rods, respectively.

The first and second toothbrush support rods are detachably coupled to the first and second rotation support shafts, respectively.

The electro-motion toothbrush further comprises an interval adjustment unit installed at the case and adjusting an interval between the first and second toothbrush support rods.

The interval adjustment unit comprises upper and lower plates respectively installed above and under the first and second rotation gears, an interval adjustment portion installed outside the case and manipulated by a user, an interval adjustment plate including a hook portion hooked by an end of the second rotation support shaft and, when the interval adjustment portion is manipulated, making the hook portion move the second rotation support shaft so that the interval between the first and second toothbrush support rods is decreased, a movement guide groove formed in the lower plate to guide movement of the second rotation support shaft, and an elastic member providing an elastic force to the second rotation support shaft to return the second rotation support shaft to an original position when the manipulation of the interval adjustment portion is completed.

The interval adjustment unit further comprises a circular movement ball which is installed at the lower surface of the upper plate to be capable of rotating and into which the second rotation support shaft is inserted.

The first rotation gear is a drive gear receiving power directly from the power source and the second rotation gear is a driven gear rotating by being engaged with the first rotation gear.

The first and second rotation gears, each having a trapezoidal profile, are engaged with each other, so that pitch diameters of the first and second rotation gears vary according to the directions of rotation shafts of the first and second rotation gears.

A human body detecting sensor detecting whether there is a contact by a hand of a user, a light emitting switch turning the light emitting unit on or off, a speed control switch controlling rotation speed of the first and second toothbrush heads, and a rotation direction change switch changing the direction of rotation of the first and second toothbrush heads, are attached at a side portion of the case. Here, a control portion which controls the power source and the light emitting unit in response to the human body detecting sensor, the light emitting switch, the speed control switch, and the rotation direction change switch, and a power supply portion which supplies power to the power source and the light emitting unit according to the control of the control portion, are provided inside the case.

The light emitting switch, the speed control switch, and the rotation direction change switch are symmetrically installed at both side portions of the case.

The electro-motion toothbrush further comprises a cleaning guide plate which includes first and second wing portions detachably coupled to the first and second toothbrush heads with a predetermined clearance and encompassing the rear side of the first and second toothbrush bristles, respectively, to protect an inner cheek of a user when the first and second toothbrush bristles rotate, and a coupling portion coupling the first and second wing portions to be capable of pivoting so that, when the toothbrush contacts an end portion of a tooth, the first and second wing portions pivot toward both side portions of the tooth and the first and second toothbrush bristles access the both side portions of the tooth.

The electro-motion toothbrush further comprises first and second coupling pins installed at first ends of the first and second wing portions in the lengthwise direction of the toothbrush heads, and first and second coupling grooves are formed at second ends of the first and second wing portions to be capable of complimentarily being coupled to the first and second coupling pins respectively, a first coupling portion coupling the first and second wing portions to be capable of pivoting when the first coupling pin installed at the first wing portion is coupled to the second coupling groove formed at the second wing portion, and a second coupling portion coupling the first and second wing portions to be capable of pivoting when the second coupling pin installed at the second wing portion is coupled to the first coupling groove formed in the first wing portion by rotating the first and second wing portions with respect to the first coupling portion in directions opposite to the rotation directions of the first and second toothbrush heads.

A plurality of protrusions and grooves are formed at the rear surfaces of the first and second wing portions so that the first and second wing portions can be engaged with each other when being rotated in directions opposite to rotation directions of the first and second toothbrush heads with respect to the first coupling portion.

The electro-motion toothbrush further comprises first and second cover plates detachably installed at the first and second wing portions to be capable of pivoting, which are separated a predetermined distance from the rear surfaces of the first and second wing portions to selectively cover the rear surfaces of the first and second wing portions.

BRIEF DESCRIPTION OF THE DRAWINGS

The above and other features and advantages of the present invention will become more apparent by describing in detail preferred embodiments thereof with reference to the attached drawings in which.

DETAILED DESCRIPTION OF THE INVENTION

Figure 1:
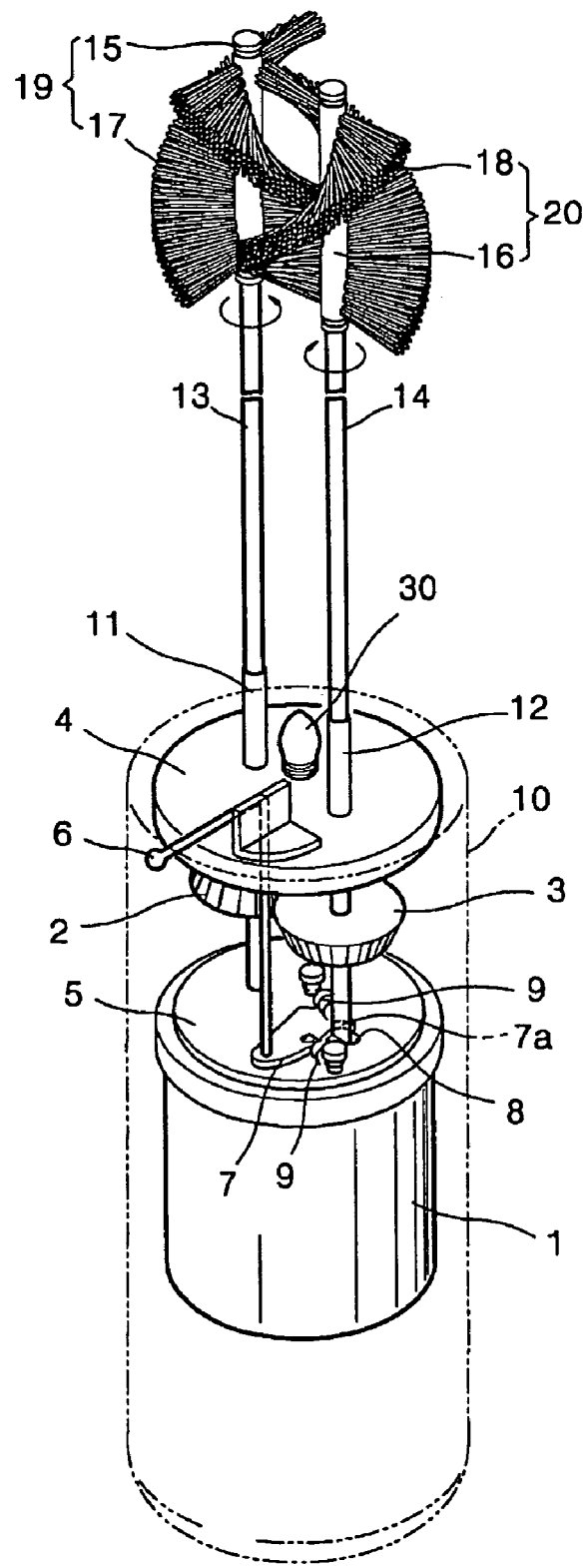
FIG. 1 is a perspective view illustrating an electro-motion toothbrush according to a preferred embodiment of the present invention.
Figure 2:
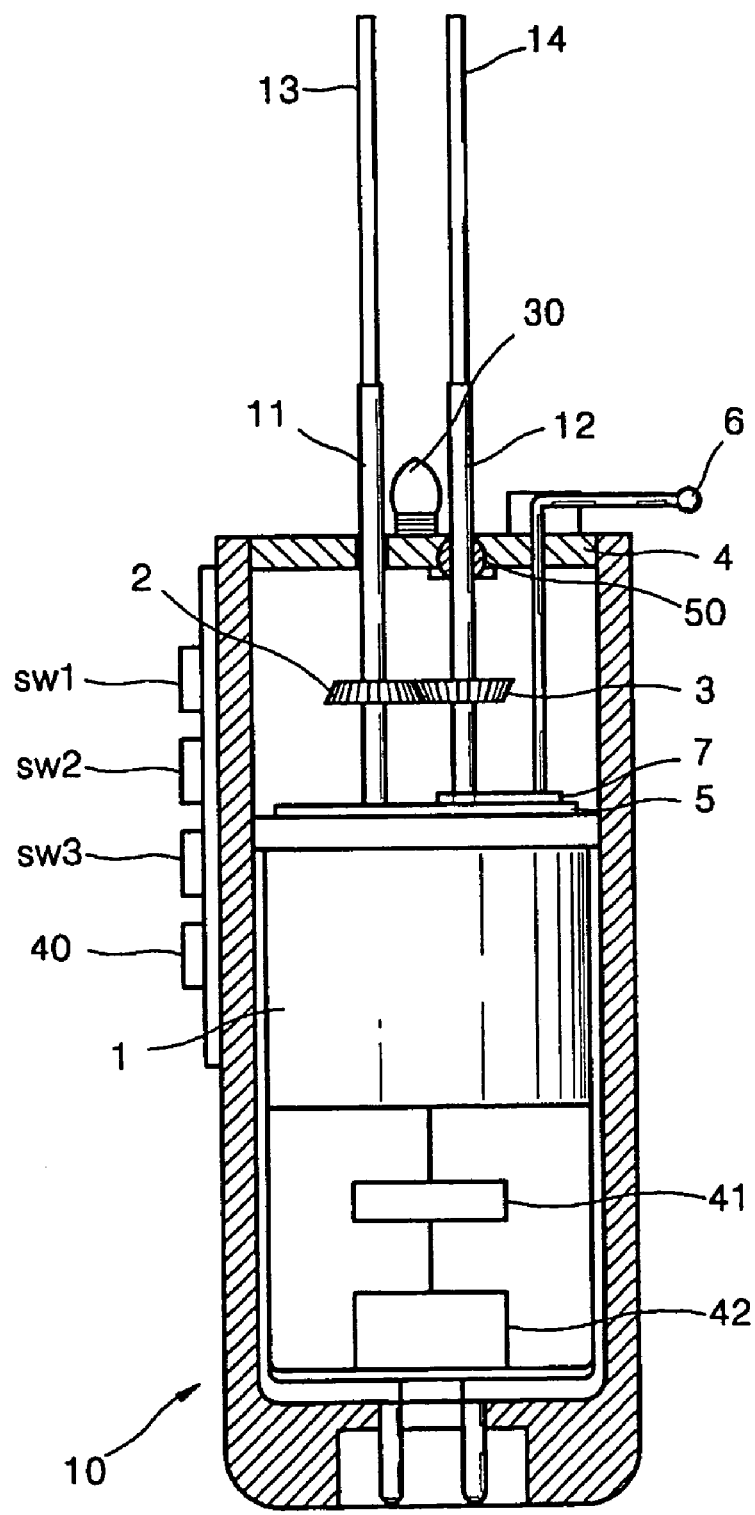
FIG. 2 is a sectional view illustrating the electro-motion toothbrush of FIG. 1.

Referring to FIGS. 1 and 2, an electro-motion toothbrush according to a preferred embodiment of the present invention includes a case 10 in which a driving unit is installed, first and second toothbrush support rods 13 and 14 which are flexible and rotate in directions different from each other by the driving unit, first and second toothbrush heads 15 and 16 connected to upper ends of the first and second toothbrush support rods 13 and 14, and first and second toothbrush bristles 17 and 18 implanted in the first and second toothbrush heads 15 and 16.

Figure 3A:
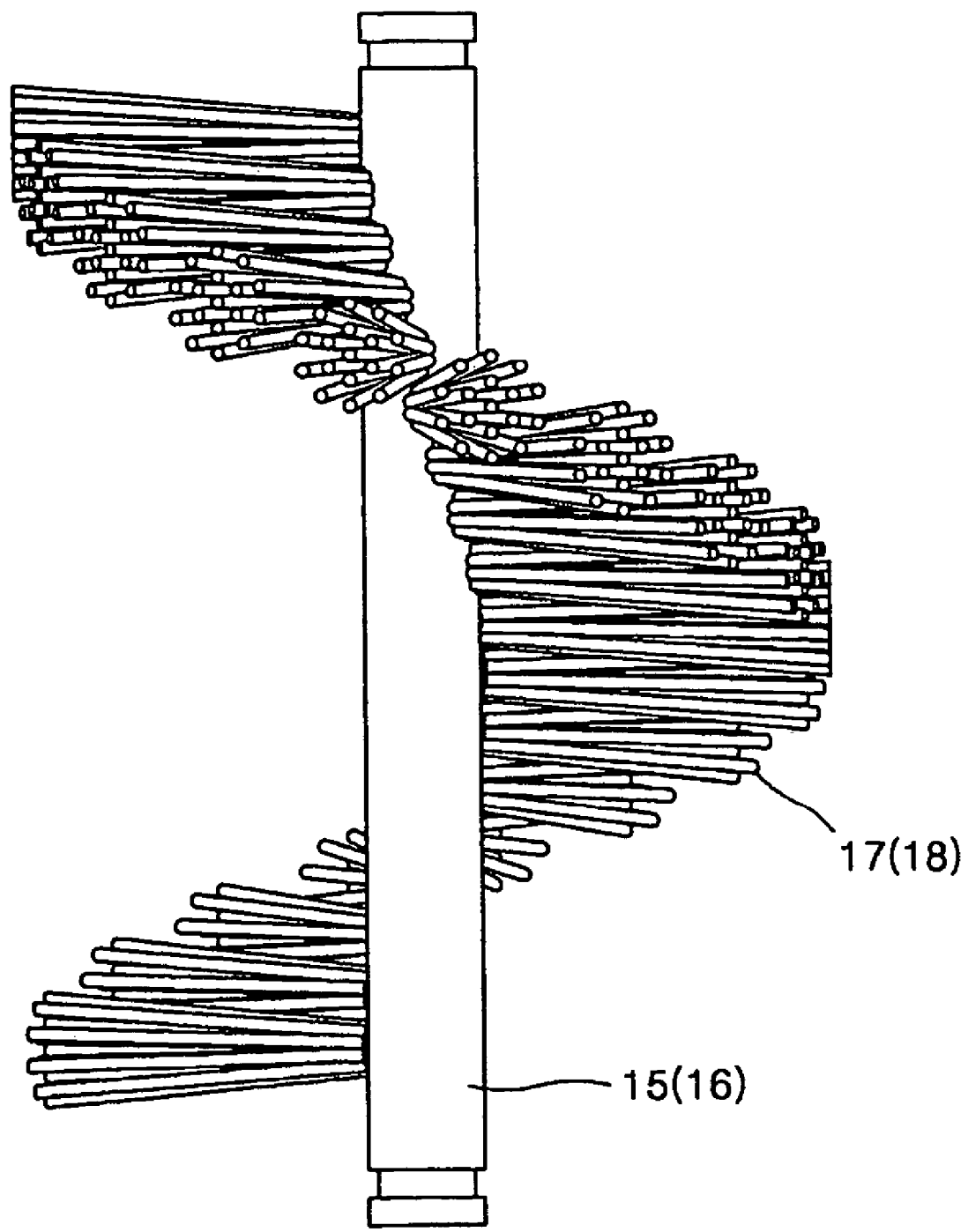
FIGS. 3A and 3B are front views illustrating preferred embodiments of the first and second toothbrush bristles shown in FIG. 1.
Figure 3B:
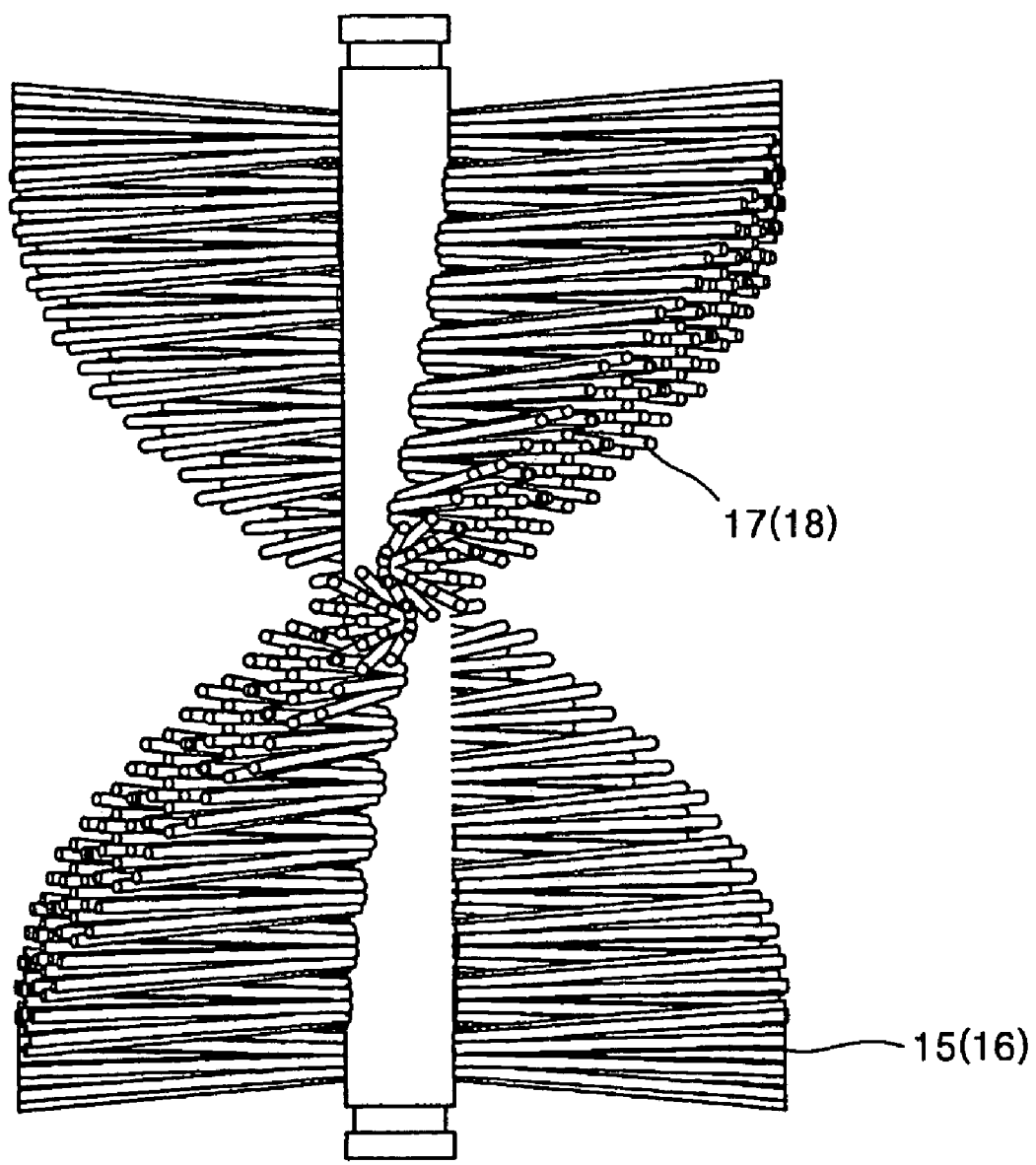

The first and second toothbrush bristles 17 and 18, as shown in FIGS. 3A and 3B, can be respectively implanted in an at least one-row spiral form to facilitate teeth access and improve teeth cleaning performance. The first and second toothbrush bristles 17 and 18 are implanted in the first and second toothbrush heads 15 and 16 in such a manner that the first and second toothbrush bristles 17 and 18 penetrate the first and second toothbrush heads 15 and 16 or the first and second toothbrush bristles 17 and 18 are respectively mounted on the surfaces of the first and second toothbrush heads 15 and 16. Here, FIG. 3A shows a state in which each of the first and second toothbrush bristles 17 and 18 is implanted in a one-row spiral form. FIG. 3B shows a state in which each of the first and second toothbrush bristles 17 and 18 is implanted in a two-row spiral form.

Figure 4A:
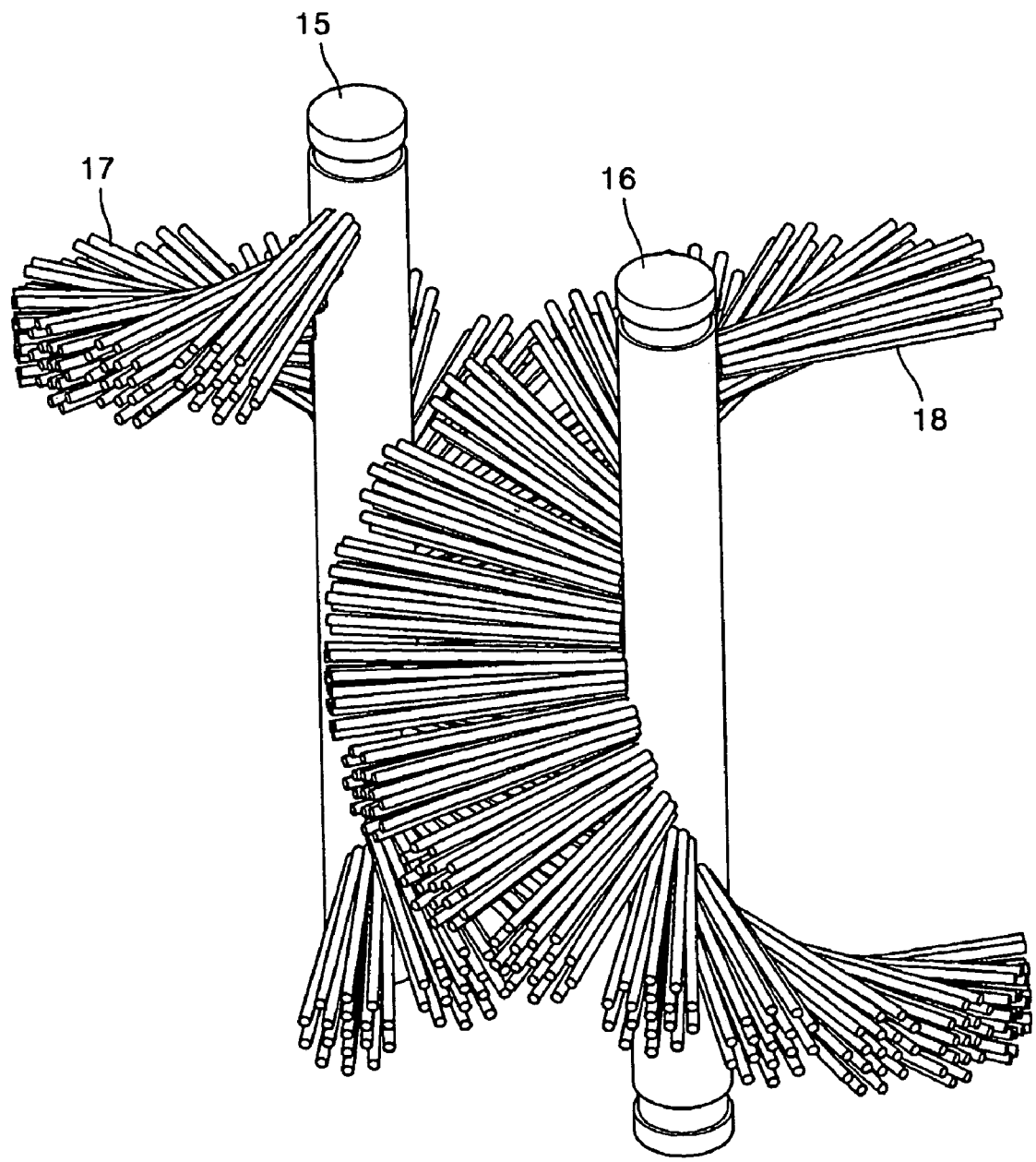
FIGS. 4A and 4B are a perspective view and a plan view, respectively, illustrating the first and second toothbrush bristles arranged in a one-row spiral form.
Figure 4B:
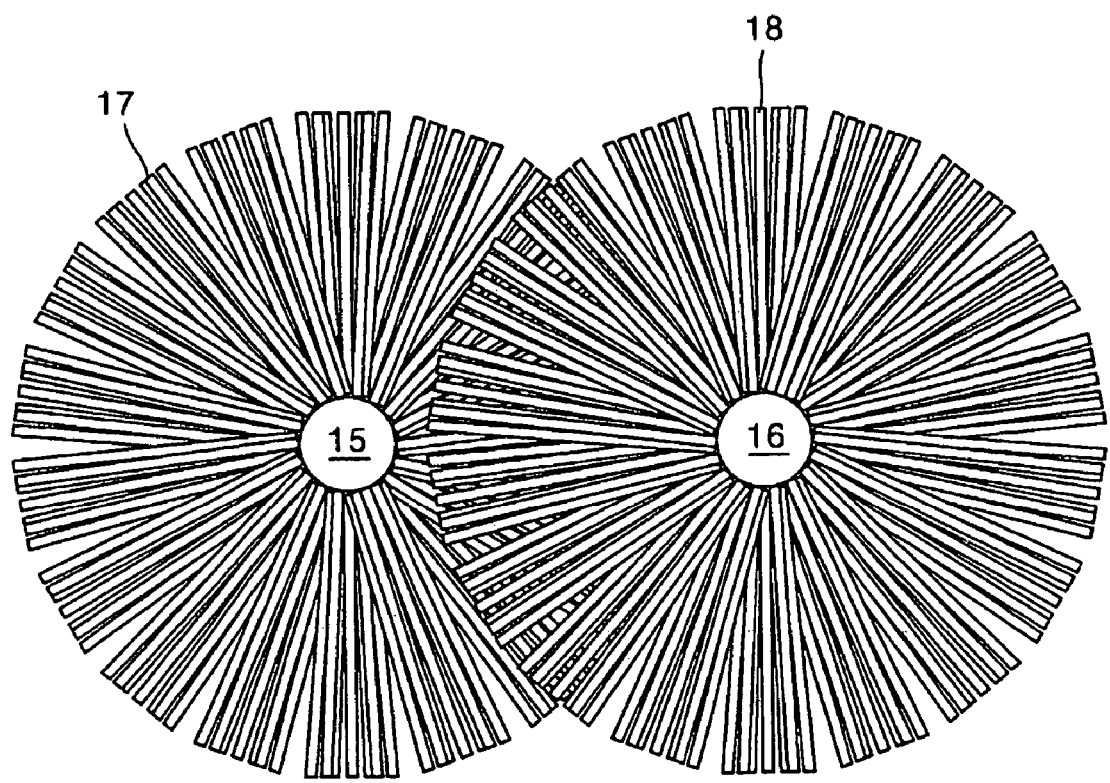
Figure 5A:
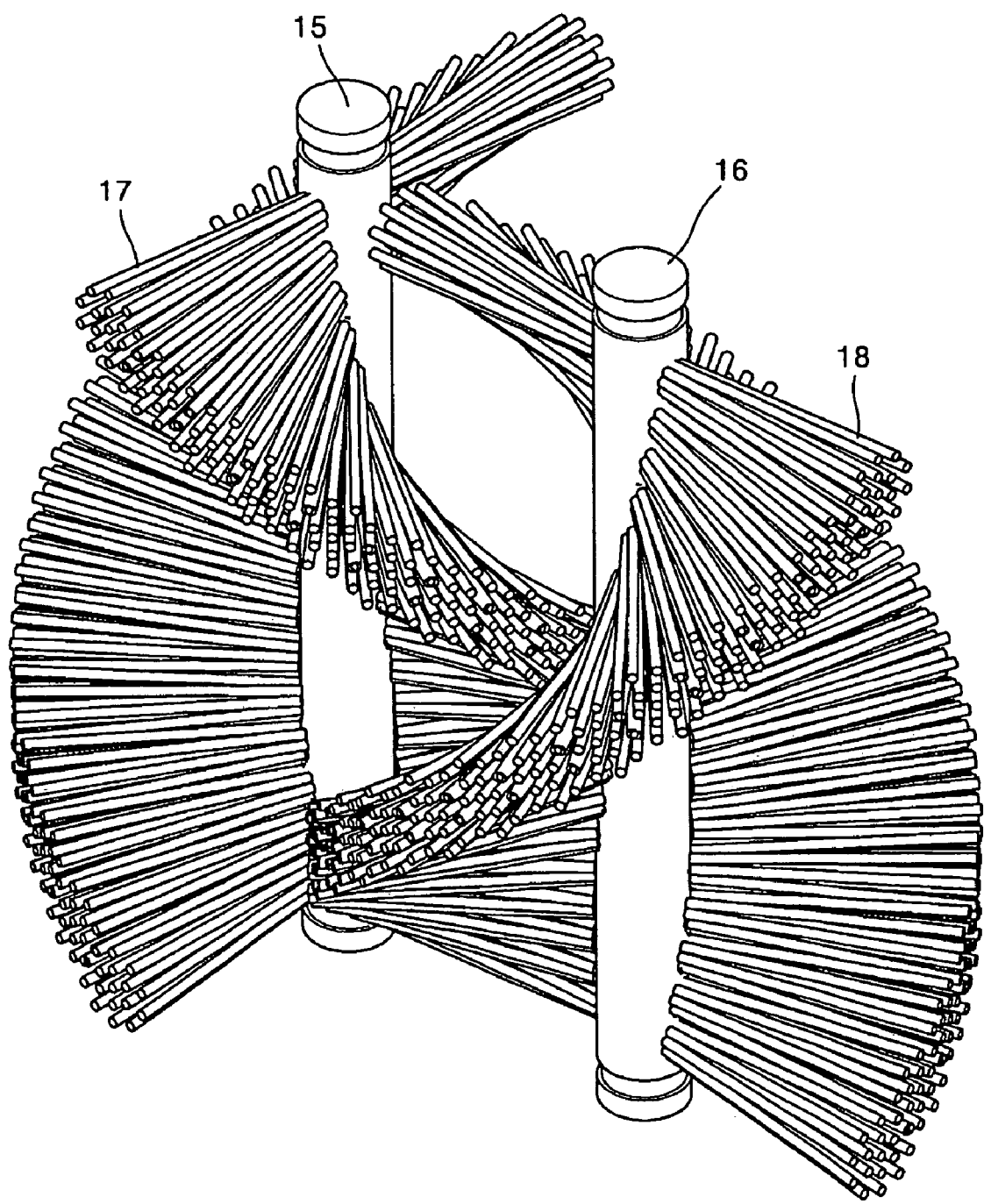
FIGS. 5A and 5B are a perspective view and a plan view, respectively, illustrating the first and second toothbrush bristles arranged in a two-row spiral form.
Figure 5B:
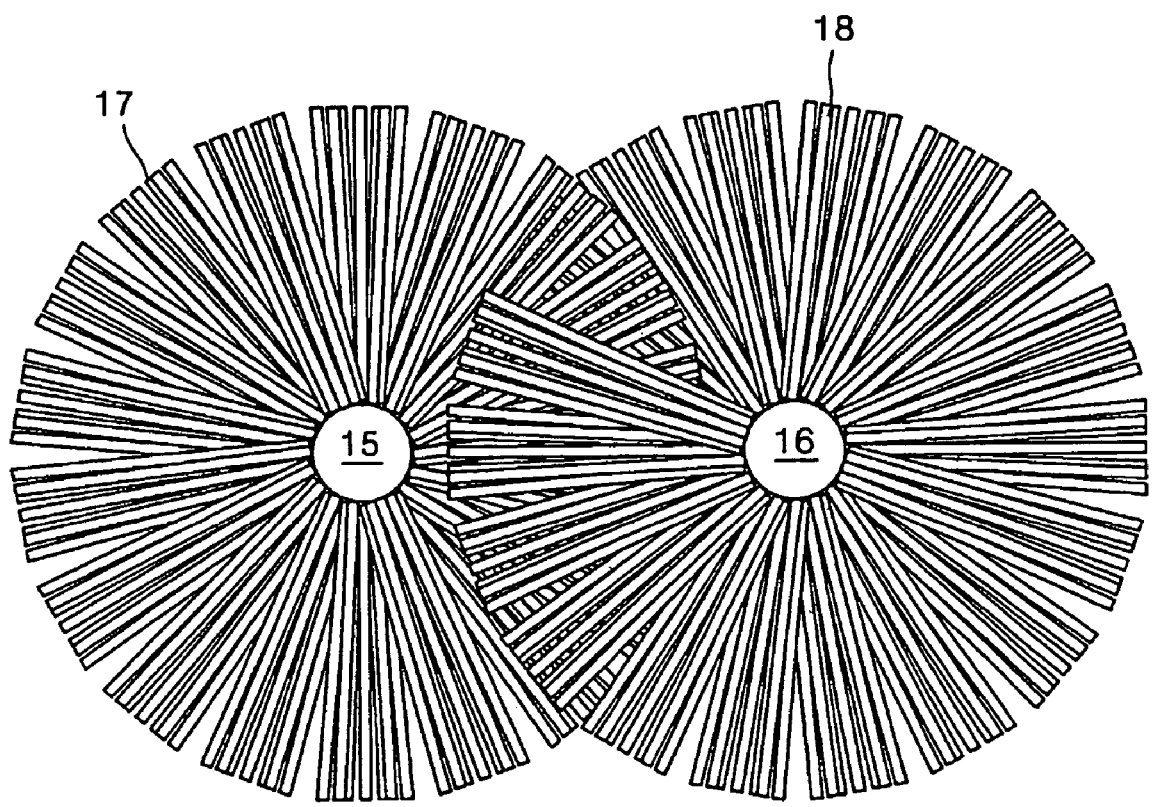

Also, as shown in FIGS. 4A, 4B, 5A, and 5B, the first and second toothbrush bristles 17 and 18 are preferably implanted to interweave with each other at upper and lower portions along the lengthwise direction of the first and second toothbrush heads 15 and 16 and do not to cross each other during rotation. Here, FIGS. 4A and 4B show the state in which the first and second toothbrush bristles 17 and 18 are implanted in a one-row spiral form. FIGS. 5A and 5B show the state in which the first and second toothbrush bristles 17 and 18 are implanted in a two-row spiral form.

Referring back to FIGS. 1 and 2, first and second toothbrush assemblies 19 and 20, formed by implanting the first and second toothbrush bristles 17 and 18 in the first and second toothbrush heads 15 and 16 are similar to each other in the upper and lower portions and are detachably installed at the first and second toothbrush heads 13 and 14, respectively. Here, the toothbrush heads 15 and 16 can be formed integrally with the toothbrush support rods 13 and 14.

The electro-motion toothbrush according to the present invention can include a light emitting unit 30 emitting light outside the case 10 to check a tooth cleaning state.

The driving unit includes a power source 1 such as a motor, first and second rotation gears 2 and 3 which are rotated by the power source 1 by being engaged with each other, and first and second rotation support shafts 11 and 12, each having one end fixed to each of the first and second rotation gears 2 and 3 and the other end connected to each of the first and second toothbrush support rods 13 and 14. Here, the first and second toothbrush support rods 13 and 14 detachably coupled to the first and second rotation support shafts 11 and 12, respectively. The first and second toothbrush support rods 13 and 14 can be integrally formed with the first and second rotation support shafts 11 and 12.

A human body detecting sensor 40 which detects whether a hand of a user contacts the apparatus, a light emitting switch SW1 which turns the light emitting unit 30 on or off, a speed control switch SW2 which controls rotation speed of the first and second toothbrush heads 15 and 16, and a rotation direction change switch SW3 which changes the rotation direction of the first and second toothbrush heads 15 and 16 according to the manipulation of the user, can be installed at the side portion of the case 10. A control portion 41 which controls the power source 1 and the light emitting unit 30 in response to the human body detecting sensor 40, the light emitting switch SW1, the speed control switch SW2, and the rotation direction change switch SW3, and a power supply portion 42 which supplies power to the power source 1 and the light emitting unit 30 according to the control of the control portion 41, can be provided inside the case 10. Also, although not shown in the drawing, a printed circuit board which electrically connects the human body detecting sensor 40, the control portion 41, the power source 1, the light emitting unit 30, the light emitting switch SW1, the speed control switch SW2, and the rotation direction change switch SW3, can be provided inside the case 10. Further, to drive the electro-motion toothbrush in a rechargeable method, a rechargeable battery (not shown), a charge pin (not shown), and a charge jack (not shown) coupled to the charge pin, can be provided inside the case 10.

Further, although FIG. 2 shows that the light emitting switch SW1, the speed control switch SW2, and the rotation direction change switch SW3 are provided only at one side portion of the case 10, the light emitting switch SW1 the speed control switch SW2, and the rotation direction change switch SW3 can be symmetrically installed at both side portions of the case 10 for the convenience of a user when the rotation directions of the first and second toothbrush heads 15 and 16 are changed by the manipulation of the user.

The electro-motion toothbrush according to the preferred embodiment of the present invention may further include an interval adjustment unit installed at the case 10 to adjust an interval between the first and second toothbrush support rods 13 and 14.

The interval adjustment unit may include upper and lower plates 4 and 5 respectively installed at the upper and lower portions of the first and second rotation gears 2 and 3, an interval adjustment portion 6 installed outside the case 10, an interval adjustment plate 7 having a hook portion 7a performing a hooking operation with one end of the second rotation support shaft 12, so that, when the interval adjustment portion 6 is operated, the hook portion 7a moves the second rotation support shaft 12 to narrow the interval between the first and second toothbrush support rods 13 and 14, a movement guide groove 8 formed at the lower plate 5 to guide the movement of the second rotation support shaft 12, and an elastic member 9 which applies an elastic force to the second rotation support shaft 12 so that it can return to the original position when the manipulation of the interval adjustment portion 6 is removed. A circular movement ball 50 is provided at the lower surface of the upper plate 4, into which the second rotation support shaft 12 is inserted, so that the second rotation support shaft 12 can freely move therein while maintaining the alignment with the second toothbrush support rod 14. Preferably, the first rotation gear 2 is a drive gear directly receiving power from the power source 1 and the second rotation gear 3 is a driven gear backlash with the first rotation gear 2. Also, to minimize reduction of a degree of engagement between the first and second rotation gears 2 and 3 due to the movement of the second rotation support shaft 12, the first and second rotation gears 2 and 3 preferably have a trapezoidal profile and are engaged with each other so that the pitch diameters of the first and second rotation gears 2 and 3 vary according to the directions of rotation shafts of the first and second rotation gears 2 and 3. Furthermore, a stopper can be further installed at the case 10 to restrict an operational range of the interval adjustment portion 6. However, since the interval adjustment unit shown in FIGS. 1 and 2 is merely an example, any units capable of adjusting the interval between the first and second toothbrush support rods 13 and 14 can be adopted as the interval adjustment unit according to the present invention.

Figure 6:
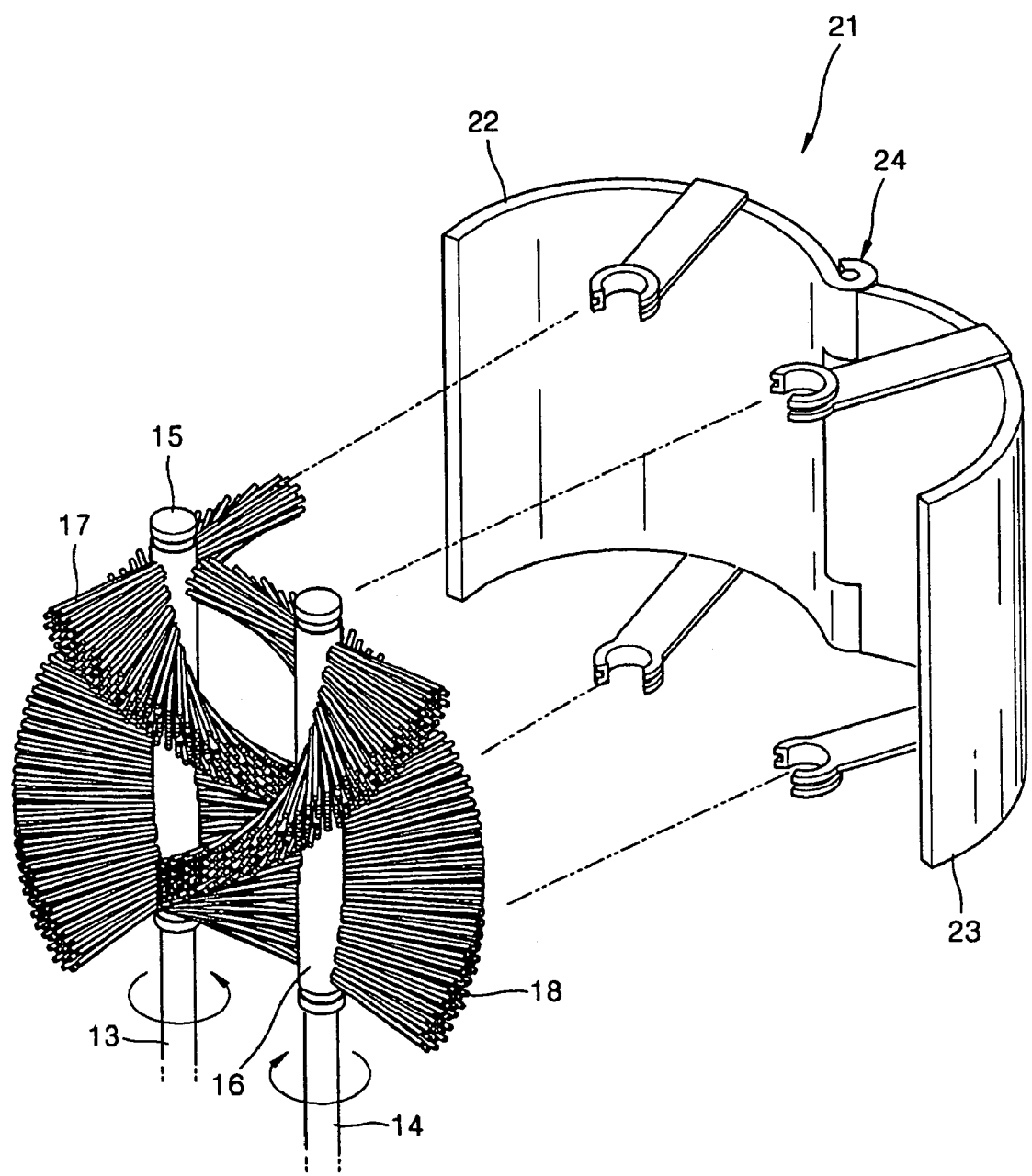
FIG. 6 is a perspective view illustrating a preferred embodiment of a cleaning guide plate coupled to the first and second toothbrush heads.

To protect the inner cheek of a user from the first and second toothbrush bristles 17 and 18 and make the direction of the first and second toothbrush bristles 17 and 18 correspond to the shape of teeth, the electro-motion toothbrush according to the preferred embodiment of the present invention may include a cleaning guide plate coupled to the first and second toothbrush heads 15 and 16, a preferred embodiment of which is shown in FIG. 6.

Referring to the drawing, the cleaning guide plate 21 may include first and second wing portions 22 and 23 detachably coupled to the first and second toothbrush heads 15 and 16 with a predetermined clearance and protecting the inner cheek during the rotation of the first and second toothbrush bristles 17 and 18 by enclosing the rear side of the first and second toothbrush bristles 17 and 18, and a coupling portion 24 which couples the first and second wing portions 22 and 23 to be capable of pivoting.

Figure 11:
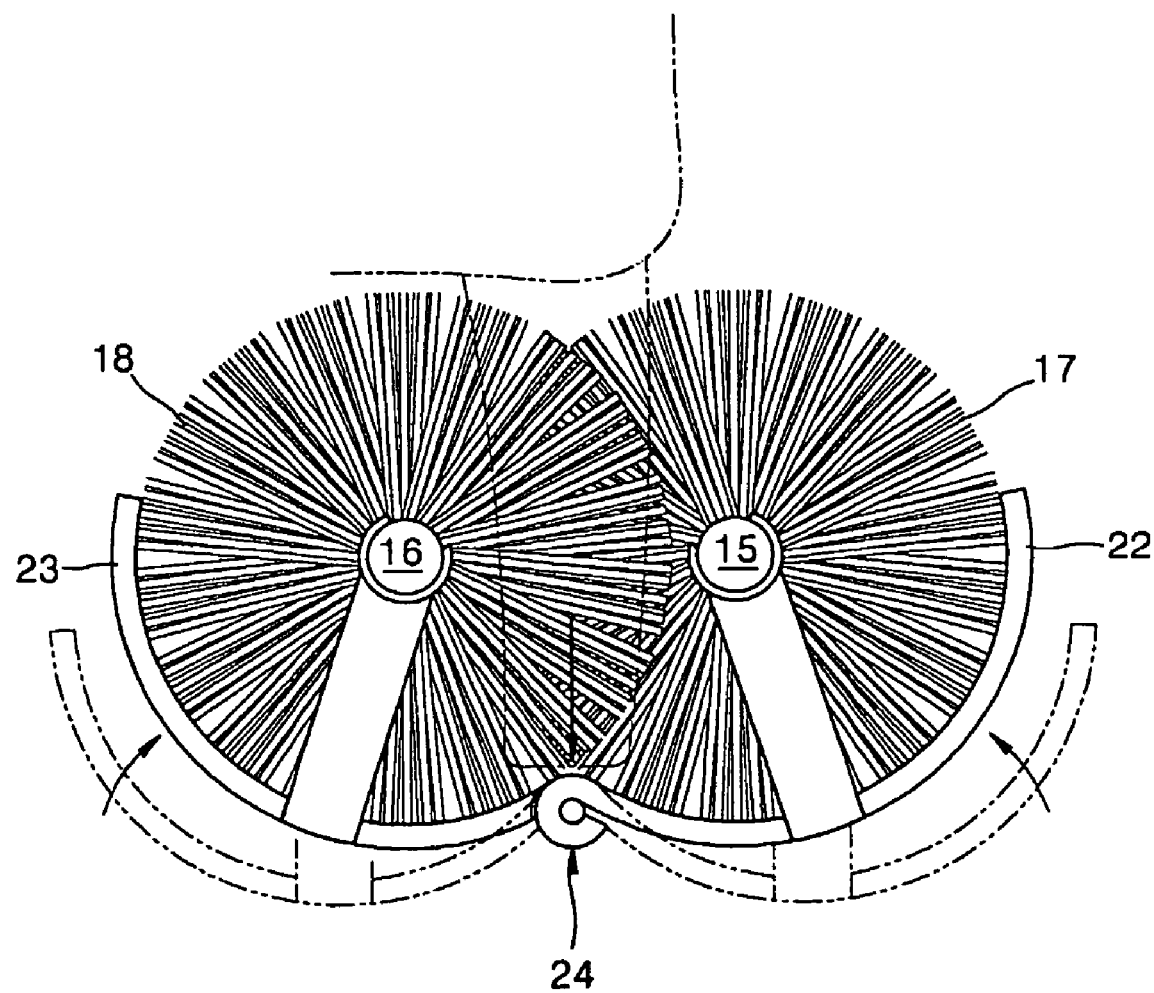
FIG. 11 is a view showing the state in which both side surfaces of an upper tooth are brushed by the electro-motion brush according to the present invention.

In the cleaning guide plate 21 having the above structure, as shown in FIG. 11, when the teeth approach the interval between the first and second toothbrush bristles 17 and 18, the first and second wing portions 22 and 23 pivot in directions in which the first and second wing portions 22 and 23 are separated from both sides of the teeth corresponding to the shape of the teeth, so that the interval between the first and second toothbrush bristles 17 and 18 is widened. When an end portion of the teeth contacts the coupling portion 24, the first and second wing portions 22 and 23 pivot toward the both side ends of the teeth so that the interval between the first and second toothbrush bristles 17 and 18 is narrowed. Thus, the interval between the first and second tooth brush bristles 17 and 18 is adjusted.

Figure 7:
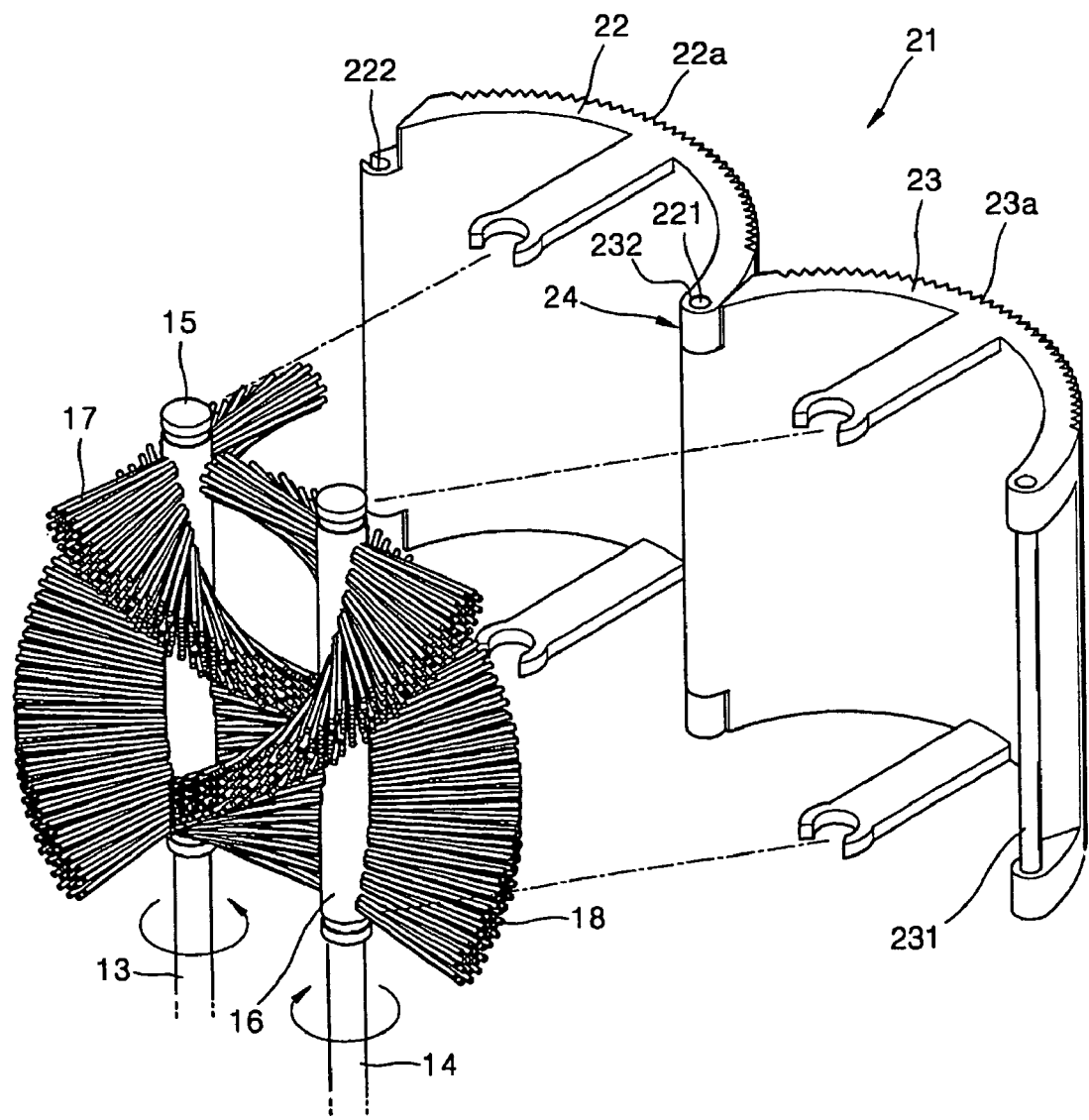
FIG. 7 is a perspective view illustrating another preferred embodiment of the cleaning guide plate.

FIG. 7 shows anther preferred embodiment of the cleaning guide plate. Referring to the drawing, first and second coupling pins 221 and 231 are installed at the end portions of the first and second wing portions 22 and 23 in the lengthwise direction of the toothbrush heads 15 and 16. First and second coupling grooves 222 and 232 can be formed at the other end portions of the first and second wing portions 22 and 23 to be capable of being coupled complementarily to the first and second coupling pins 221 and 231, respectively. A plurality of protrusions and grooves 22a and 23a are formed at the rear surfaces of the first and second wing portions 22 and 23 to be capable of being engaged with each other when the first and second wing portions 22 and 23 are rotated in directions opposite to the rotation directions of the first and second toothbrush heads 15 and 16 with respect to the coupling portion 24.

Figure 8:
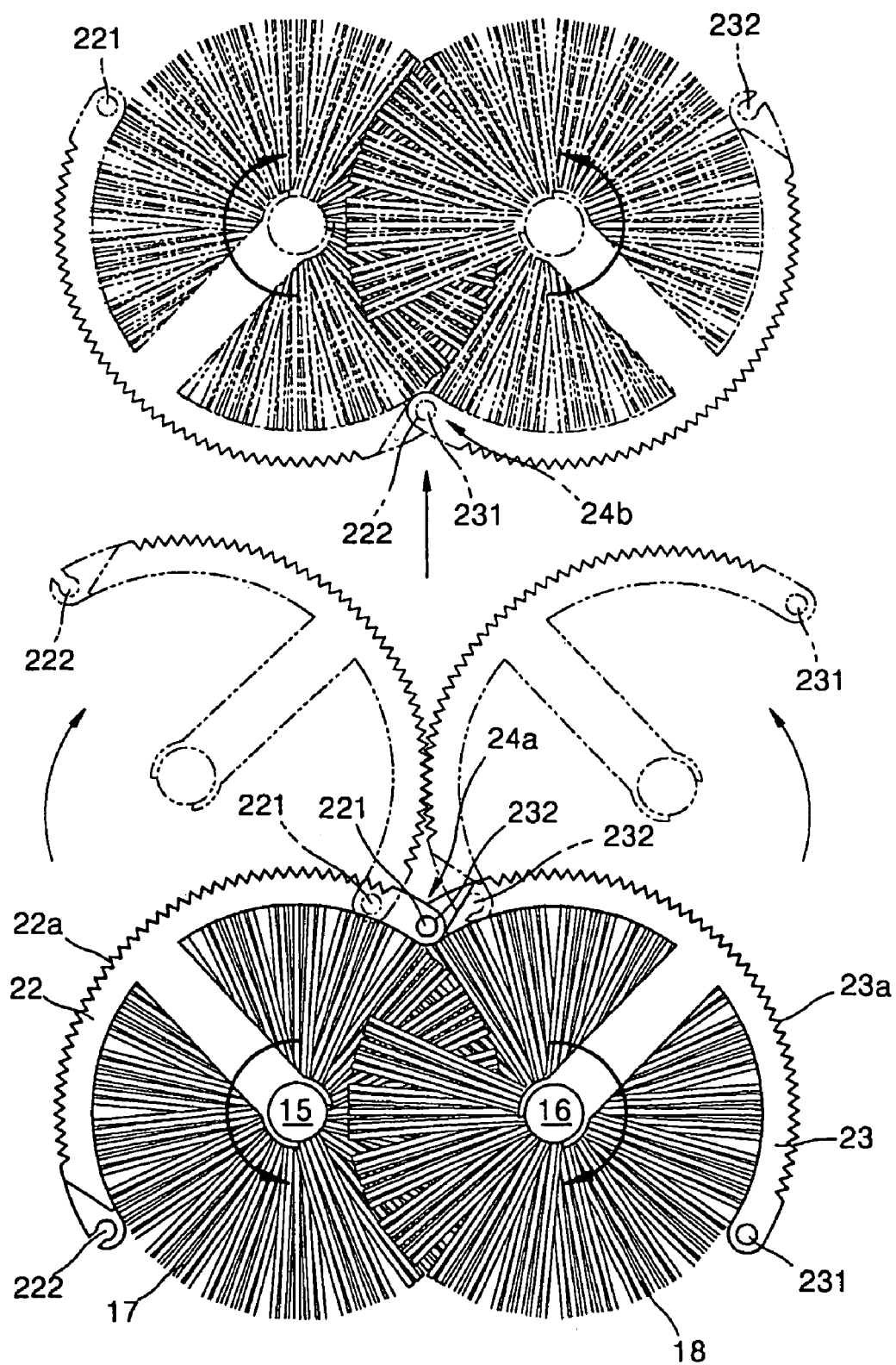
FIG. 8 is a view for explaining the operation of the cleaning guide plate shown in FIG. 7.

In the cleaning guide plate 21 having the above structure, as shown in FIG. 8, when the first coupling pin 221 installed at the first wing portion 22 is coupled to the second coupling groove 232 formed in the second wing portion 23, a first coupling portion 24a coupling the first and second wing portions 22 and 23 to be capable of pivoting is formed. When the first and second wing portions 22 and 23 are rotated with respect to the first coupling portion 24a in directions opposite to the rotation directions of the first and second toothbrush heads 15 and 16 to couple the second coupling pin 231 installed at the second wing portion 23 to the first coupling grove 222 formed in the first wing portion 22, a second coupling portion 24b coupling the first and second wing portions 22 and 23 to be capable of pivoting is formed.

Figure 9:
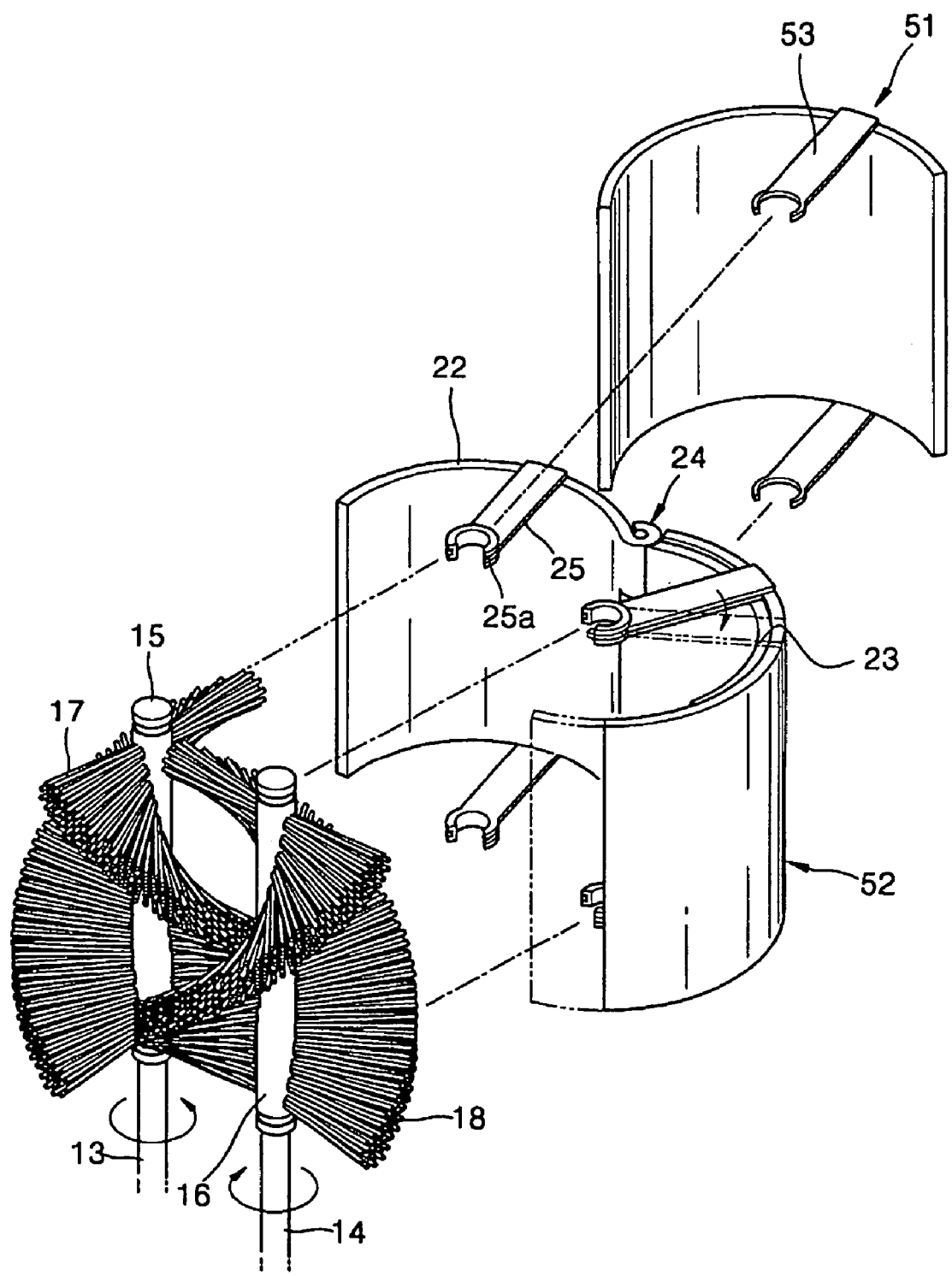
FIG. 9 is a perspective view illustrating a preferred embodiment of first and second cover plates coupled to the cleaning guide plate.

To protect a user from the rotating first and second toothbrush bristles 17 and 18, the electro-motion toothbrush according to the present preferred embodiment of the present invention can include first and second cover plates respectively installed at the rear surfaces of the first and second cover plate. FIG. 9 shows the first and second cover plates according to a preferred embodiment of the present invention.

As shown in the drawing, first and second cover plates 51 and 52 are separated a predetermined distance from the rear surfaces of the first and second wing portions 22 and 23 and detachably installed at the first and second wing portions 22 and 23 to be capable of pivoting to selectively cover the rear surfaces of the first and second wing portions 22 and 23. Here, a slide groove 25a is formed in a ring coupling portion 25 to couple the first and second wind portions 22 and 23 to the first and second toothbrush heads 15 and 16. A coupling portion 53 extending from each of the first and second cover plates 51 and 52 is coupled to the slide groove 25a. Thus, the first and second cover plates 51 and 52 can be detachably installed at the first and second wing portions 22 and 23 to be capable of pivoting. However, since the coupling structure of the first and second cover plates 51 and 52 and the first and second wing portions 22 and 23 shown in FIG. 9 is merely an example, the present invention is not limited thereto.

Although not shown in the drawings, for the safety of a user, an additional cover member encompassing outside the first and second toothbrush support rods 13 and 14 that are rotating can be provided in the electro-motion toothbrush according to the present invention. The cover member can be integrally formed with the cleaning guide plate 21.

Figure 10:
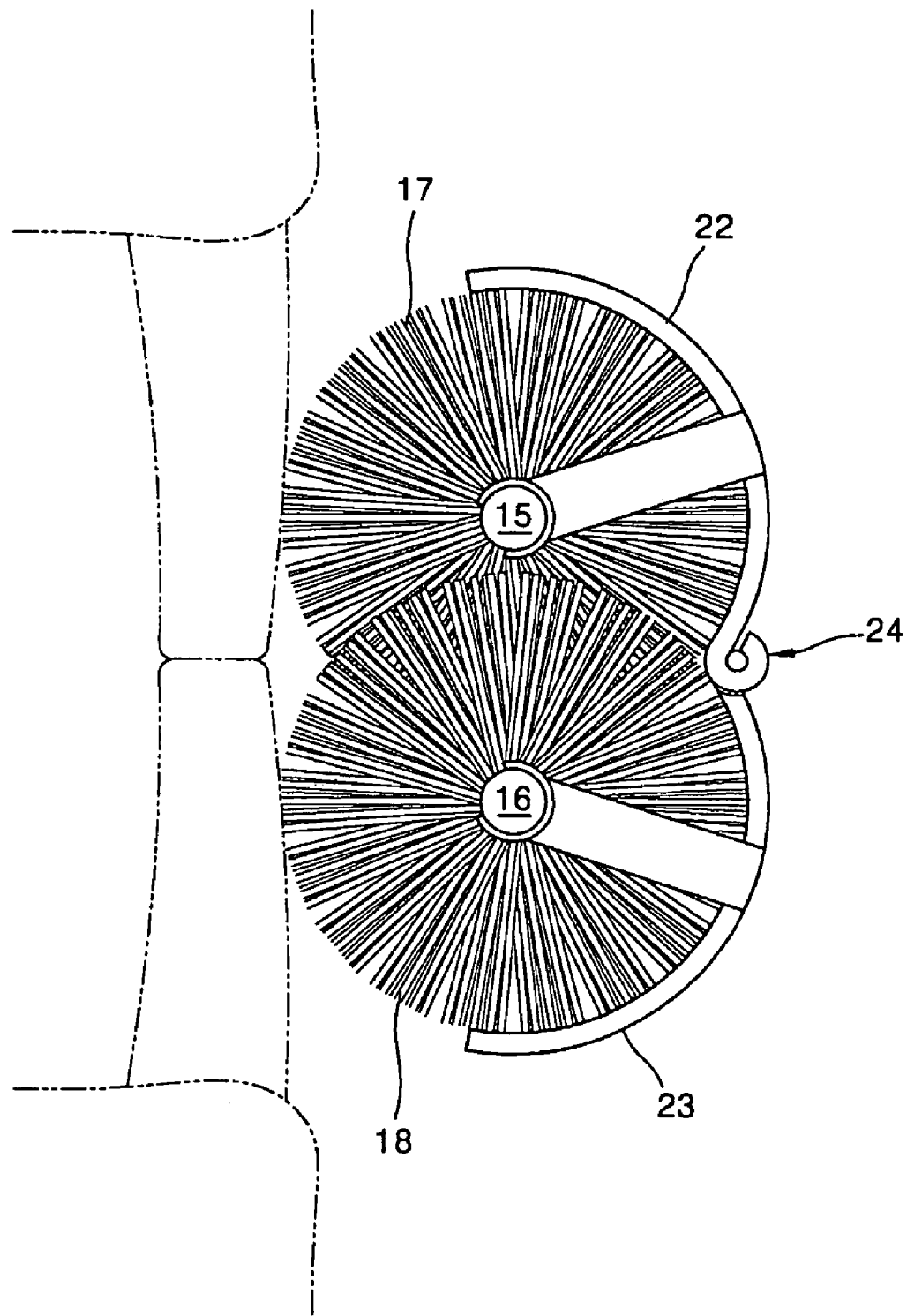
FIG. 10 is a view showing the state in which one side surface of upper and lower teeth is brushed by the electro-motion brush according to the present invention.
Figure 12:
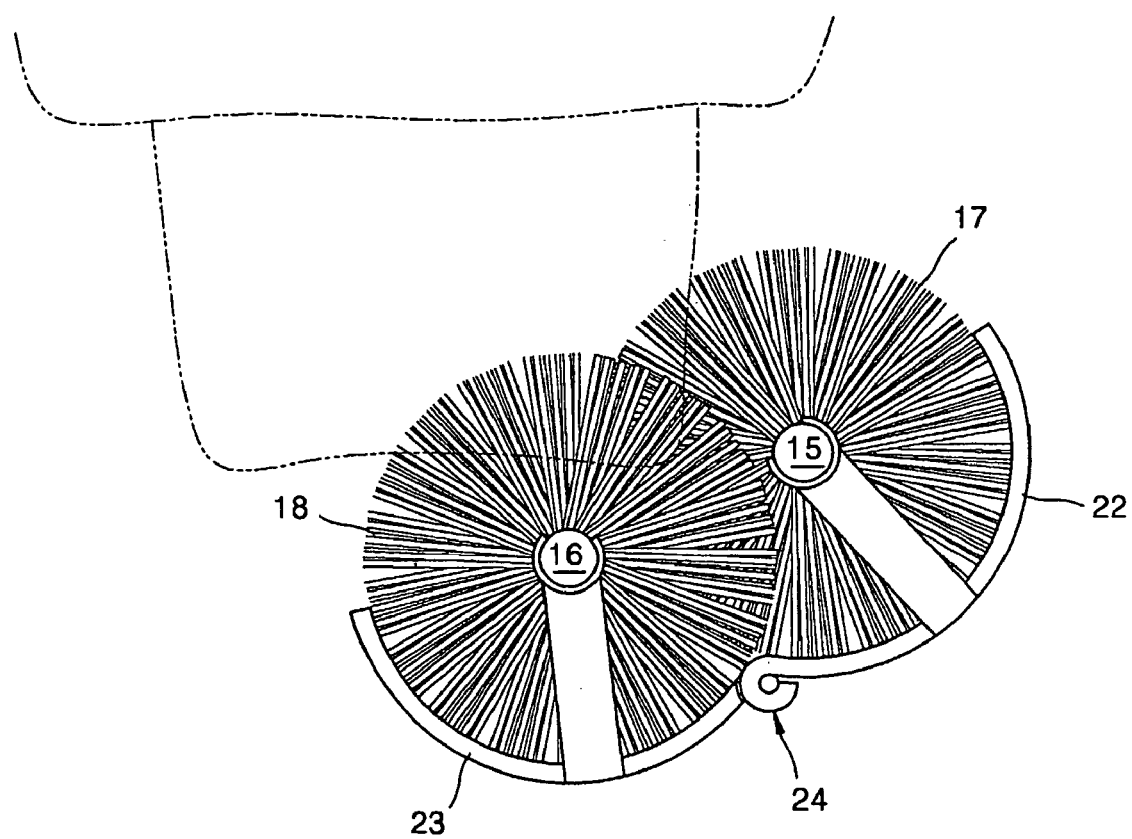
FIG. 12 is a view showing the state in which a biting surface and a side surface of a tooth are brushed by the electro-motion brush according to the present invention.

According to the electro-motion toothbrush according to the preferred embodiment of the present invention, since the first and second toothbrush support rods 13 and 14 are flexible, as shown in FIGS. 10, through 12, when one side surface of the upper and lower teeth, both side surfaces of a tooth, and a biting surface of a tooth are brushed, the first and second toothbrush bristles 17 and 18 can easily access the teeth. Also, since the first and second toothbrush bristles 17 and 18 are implanted to interweave with each other at the upper and lower portions to be capable of rotating in a state of not crossing each other, the toothbrush bristles 17 and 18 can easily access the interval between teeth.

While this invention has been particularly shown and described with reference to preferred embodiments thereof, it will be understood by those skilled in the art that various changes in form and details may be made therein without departing from the spirit and scope of the invention as defined by the appended claims.

As described above, according to the electro-motion toothbrush according to the present invention, since the toothbrush support rods are flexible and the toothbrush bristles are implanted to interweave with each other at the upper and lower portions to be capable of rotating in a state of not crossing each other, the toothbrush bristles can easily access the interval between teeth and not only both side surfaces of the teeth but also one side surface of the upper and lower teeth, and a side surface and a biting surface of a tooth according to the teeth arrangement and shape can be properly brushed.

Also, since the interval between the toothbrush support rods can be adjusted by a user, although the thickness of a tooth is different from user to user, no inconvenience exist in brushing the teeth.

Furthermore, while the cleaning guide plate and the cover plate are provided to improve safety of a user, since the power source is turned on or off by the detection operation of the human body detecting sensor, convenience in use is improved.

Furthermore, when the toothbrush bristles are deformed due to a long-term use, since the electro-motion toothbrush can be used by changing the rotation direction of the toothbrush bristles, inconvenience of frequently replacing toothbrush heads is removed.

What is claimed is:

1. An electro-motion toothbrush comprising:
   a case containing a driving unit, the driving unit including;
      a power source,
      first and second rotation gears which engage each other and are rotated by power from the power source, and
      first and second rotation support shafts, connected to and activated through first ends fixed to the first and second rotation gears, respectively, and having second ends;
   first and second toothbrush support rods which are flexible and rotated by the driving unit in directions opposite to each other, wherein the second ends of the first and second rotation support shafts are connected to the first and second toothbrush support rods, respectively;
   first and second toothbrush heads connected to ends of the first and second toothbrush support rods, respectively;
   first and second toothbrush bristles implanted along a lengthwise direction of the first and second toothbrush heads, which interweave with each other, and which do not cross each other during rotation of the first and second toothbrush support rods; and
   an interval adjustment unit installed at the case and adjusting spacing between the first and second toothbrush support rods.

2. The electro-motion toothbrush as claimed in claim 1, wherein the interval adjustment unit comprises:
   upper and lower plates respectively installed on opposite sides of the first and second rotation gears;
   an interval adjustment portion located outside the ease for manipulation by a user;
   an interval adjustment plate including a hook portion hooked by an end of the second rotation support shaft and, when the interval adjustment portion is manipulated, making the hook portion move the second rotation support shaft so that the spacing between the first and second toothbrush support rods is changed;
   a movement guide groove in the lower plate guiding movement of the second rotation support shaft; and
   an elastic member providing an elastic force to the second rotation support shaft to return the second rotation support shaft to an original position when the manipulation of the interval adjustment portion is completed.

3. The electro-motion toothbrush as claimed in claim 2, wherein the interval adjustment unit further comprises a circular movement ball, at the lower surface of the upper plate and rotating, and into which the second rotation support shaft is inserted.

4. The electro-motion toothbrush as claimed in claim 2, wherein the first rotation gear is a drive gear receiving power directly from the power source and the second rotation gear is a driven gear rotating by being engaged with the first rotation gear.

5. The electro-motion toothbrush as claimed in claim 2, wherein the first and second rotation gears each have a trapezoidal profile, and pitch diameters of the first and second rotation gears vary according to directions of rotation shafts of the first and second rotation gears.

6. The electro-motion toothbrush as claimed in claim 1, including:
   a light emitting unit which emits light outside the case;
   a human body detecting sensor detecting whether there is contact by a hand of a user, a light emitting switch turning the light emitting unit on and off, a speed control switch controlling rotation speed of the first and second toothbrush heads, and a rotation direction change switch changing the direction of rotation of the first and second toothbrush heads, attached at a side of the case;
   a control which controls the power source and the light emitting unit in response to the human body detecting sensor, the light emitting switch, the speed control switch, and the rotation direction change switch; and
   a power supply which supplies power to the power source and the light emitting unit according to the control of the control, located inside the case.

7. The electro-motion toothbrush as claimed in claim 6, wherein the light emitting switch, the speed control switch, and the rotation direction change switch are symmetrically located at opposite sides of the case.

8. The electro-motion toothbrush as claimed in claim 1, wherein the first and second toothbrush bristles are implanted in an at least one spiral row.

9. The electro-motion toothbrush as claimed in claim 1, further comprising a light emitting unit which emits light outside the case.

10. The electro-motion toothbrush as claimed in claim 1, wherein the first and second toothbrush support rods are detachably coupled to the first and second rotation support shafts, respectively.

11. An electro-motion toothbrush comprising:
   a case containing a driving unit;
   first and second toothbrush support rods which are flexible and rotated by the driving unit in directions opposite to each other;
   first and second toothbrush heads connected to ends of the first and second toothbrush support rods, respectively;
   first and second toothbrush bristles implanted along a lengthwise direction of the first and second toothbrush heads, which interweave with each other, and which do not cross each other during rotation of the first and second toothbrush support rods; and
   a cleaning guide plate including
      first and second wing portions detachabty coupled to the first and second toothbrush heads with a predetermined clearance and encompassing a rear side of the first and second toothbrush bristles, respectively, to protect an inner cheek of a user when the first and second toothbrush bristles rotate, and
      a coupling portion coupling the first and second wing portions for pivoting so that, when the toothbrush contacts an end of a tooth, the first and second wing portions pivot toward opposite sides of the tooth and the first and second toothbrush bristles access the opposite sides of the tooth.

12. The electro-motion toothbrush as claimed in claim, 11 including first and second toothbrush assemblies of the first and second toothbrush bristles implanted in the first and second toothbrush heads, respectively, which are similar to each other in upper and lower sides and are detachably coupled to the first and second toothbrush support rods, respectively.

13. The electro-motion toothbrush as claimed in claim 11, further comprising
   first and second coupling pins located at first ends of the first and second wing portions, in the lengthwise direction of the toothbrush heads, and first and second coupling grooves at second ends of the first and second wing portions complementarily coupled to the first and second coupling pins, respectively,
   a first coupling portion coupling the first and second wing portions for pivoting when the first coupling pin located at the first wing portion is coupled to the second coupling groove located at the second wing portion, and
   a second coupling portion coupling the first and second wing portions for pivoting when the second coupling pin located at the second wing portion is coupled to the first coupling groove located in the first wing portion, by rotating the first and second wing portions with respect to the first coupling portion in directions opposite to rotation directions of the first and second toothbrush heads.

14. The electro-motion toothbrush as claimed in claim 13, including a plurality of protrusions and grooves at the rear surfaces of the first and second wing portions so that the first and second wing portions can engage each other when being rotated in directions opposite to the rotation directions of the first and second toothbrush heads, with respect to the first coupling portion.

15. The electro-motion toothbrush as claimed in claim 11, further comprising first and second cover plates detachably installed at the first and second wing portions for pivoting, and separated a predetermined distance from the rear surfaces of the first and second wing portions, for selectively covering rear surfaces of the first and second wing portions.

16. The electro-motion toothbrush as claimed in claim 11, wherein the first and second toothbrush bristles are implanted in an at least one spiral row.

17. The electro-motion toothbrush as claimed in claim 11, further comprising a light emitting unit which emits light outside the case.

18. The electro-motion toothbrush as claimed in claim 11, wherein the driving unit comprises:
   a power source;
   first and second rotation gears which engage each other and are rotated by power from the power source; and
   first and second rotation support shafts, connected to and activated though first ends fixed to the first and second rotation gears, respectively, and having second ends connected to the first and second toothbrush support rods, respectively.

19. The etectro-motion toothbrush as claimed in claim 18, wherein the first and second toothbrush support rods are detachably coupled to the first and second rotation support shafts, respectively.

20. The electro-motion toothbrush as claimed in claim 18, including:
   a light emitting unit which emits light outside the case;
   a human body detecting sensor detecting whether there is contact by a hand of a user, a light emitting switch turning the light emitting unit on and off, a speed control switch controlling rotation speed of the first and second toothbrush heads, and a rotation direction change switch changing the direction of rotation of the first and second toothbrush heads, attached at a side of the case;

a control which controls the power source and the light emitting unit in response to the human body detecting sensor, the light emitting switch, the speed control switch, and the rotation direction change switch; and a power supply which supplies power to the power source and the light emitting unit according to the control of the control, located inside the case.

21. The electro-motion toothbrush as claimed in claim 20, wherein the light emitting switch, the speed control switch, and the rotation direction change switch are symmetrically located at opposite sides of the case.

* * * * *